United States Patent [19]

Dieterich

[11] 4,282,147

[45] Aug. 4, 1981

[54] DISPERSION OF AROMATIC ISOCYANATOSULFONIC ACID URETDIONES IN ORGANIC POLYISOCYANATES AND A PROCESS FOR THEIR PREPARATION

[75] Inventor: Dieter Dieterich, Leverkusen, Fed. Rep. of Germany

[73] Assignee: Bayer Aktiengesellschaft, Leverkusen, Fed. Rep. of Germany

[21] Appl. No.: 94,414

[22] Filed: Nov. 15, 1979

[30] Foreign Application Priority Data

Nov. 28, 1978 [DE] Fed. Rep. of Germany ....... 2851341

[51] Int. Cl.$^3$ .................... C07D 229/00; C08G 18/78
[52] U.S. Cl. ................................ 260/239 A; 252/182
[58] Field of Search ............... 260/453 AR, 453 SP, 260/239 A; 528/71, 73; 521/161, 162; 252/182

[56] References Cited

U.S. PATENT DOCUMENTS

| 3,826,769 | 7/1974 | Carlson ..................... 260/29.2 TN |
| 3,959,329 | 5/1976 | Dietrich et al. .............. 260/453 AR |
| 4,119,658 | 10/1978 | Dieterich ..................... 260/453 AR |
| 4,143,062 | 3/1979 | Dieterich ..................... 260/453 SP |
| 4,225,532 | 9/1980 | Dieterich et al. ............. 260/453 SP |

FOREIGN PATENT DOCUMENTS

| 2651065 | 5/1978 | Fed. Rep. of Germany . |
| 2735047 | 2/1979 | Fed. Rep. of Germany . |
| 1494467 | 12/1977 | United Kingdom . |

*Primary Examiner*—Dolph H. Torrence
*Attorney, Agent, or Firm*—Gene Harsh; Joseph C. Gil

[57] ABSTRACT

The instant invention is directed to non-sedimenting dispersions of finely divided solid aromatic isocyanatosulfonic acid uretdiones in non-sulfonic polyisocyanates and a process for their preparation.

9 Claims, No Drawings

DISPERSION OF AROMATIC ISOCYANATOSULFONIC ACID URETDIONES IN ORGANIC POLYISOCYANATES AND A PROCESS FOR THEIR PREPARATION

BACKGROUND OF THE INVENTION

Solid isocyanatosulfonic acid uretdiones are obtained by the sulfonation of aromatic isocyanates, in liquid form or in solution in organic solvents, generally accumulating in the form of coarse-grained suspensions (cf. for example German Offenlegungsschrift No. 2,524,476). By filtering the suspensions, it is possible to recover the isocyanatosulfonic acid uretdiones in powder form. In many cases, the suspensions of isocyanatosulfonic acid uretdiones in isocyanate or even in organic solvents which are obtained during sulfonation are used for further reactions of the isocyanatosulfonic acids, for example with oxiranes or oxetanes (cf. for example German Offenlegungsschrift No. 2,651,065 or German Offenlegungsschrift No. 2,735,047). Difficulties are involved in handling these suspensions on account of their tendency to sediment. Exact metering is virtually impossible. In addition, the fact that the isocyanatosulfonic acids are characterized by being in a coarse dispersion reduces their reactivity to oxiranes and oxetanes. This results in the production of foams wherein the dispersed phase is not dissolved quickly enough. This applies in particular to suspensions of the dimeric sulfonic acid of isocyanatotoluene or diisocyanatodiphenyl methane in excess tolyene diisocyanate or diisocyanatodiphenyl methane.

Accordingly, the object of the present invention is to provide non-sedimenting dispersions of aromatic isocyanatosulfonic acid uretdiones which do not have any of the disadvantages referred to above.

According to the present invention, this object is achieved for the first time by the process described in detail hereinafter.

DESCRIPTION OF THE INVENTION

The present invention relates to finely divided, non-sedimenting dispersions in organic polyisocyanates of finely divided, solid aromatic isocyanatosulfonic acid uretdiones having a mean particle size of less than 0.02 mm which are liquid at room temperature or which can be liquefied by heating to at most 60° C. and which contain a total of from 5 to 60 equivalent percent of free and dimerized isocyanate groups of aromatic polyisocyanatosulfonic acids, based on the total number of equivalents of isocyanate groups.

The present invention also relates to a process for producing dispersions such as these by sulfonating aromatic polyisocyanates, characterized in that:

(a) aromatic polyisocyanates are sulfonated with from 5 to 60 mol % of sulfur trioxide or with a corresponding quantity of sulfonating agent containing or forming sulfur trioxide in the presence of from 0.2 to 25% by weight, based on the weight of the polyisocyanate, of a hydrophobic organic substance which is free from hydrophilic substituents inert to isocyanate groups, is soluble in isocyanates at least at an elevated temperature, is solid or liquid at room temperature and contains polar groups and, optionally, contains isocyanate-reactive groups, or (b) aromatic polyisocyanates are sulfonated with from 20 to 200 mol % of sulfur trioxide or with a corresponding quantity of a sulfonating agent containing or forming sulfur trioxide in the presence of from 0.2 to 25% by weight, based on the weight of the polyisocyanate, of an organic substance of the type mentioned in (a) in inert low-boiling organic solvents, followed by removal of the solvent by distillation, the polyisocyanate forming the major part of the continuous phase being added before removal of the solvent by distillation in cases where more than 60 mol % of sulfur trioxide are used per mol of polyisocyanate, or (c) unstable coarse suspensions of aromatic isocyanatosulfonic acid uretdiones in polyisocyanates or inert solvents are briefly heated to at most 150° C. in the presence of from 0.2 to 25% by weight, based on the total quantity of isocyanate, of organic substances of the type defined in (a) until a solution is formed, followed by rapid cooling and/or grinding, the organic solvent used, if any, being removed by distillation and, in cases where coarse suspensions which do not contain any non-sulfonated polyisocyanates, are used, the organic polyisocyanate which forms the continuous phase being added before removal of the solvent by distillation and the aromatic isocyanatosulfonic acid uretdione and the non-sulfonated polyisocyanate being used in such quantities that the stable dispersions ultimately obtained contain a total of from 5 to 60 equivalent percent of free and dimerized isocyanate groups of the isocyanatosulfonic acid uretdione, based on the total number of equivalents of isocyanate groups.

German Offenlegungsschrift No. 2,640,103 and U.S. Pat. No. 4,143,062 describe the production of suspensions of isocyanatosulfonic acids in certain suspending agents. On page 8 of the Offenlegungsschrift, it is pointed out that the addition of surfactants generally leads to a reduction in particle size. In view of this prior art, it was particularly surprising to find that non-sedimenting dispersions of aromatic isocyanatosulfonic acid uretdiones in organic polyisocyanates, as the continuous phase, can be produced using hydrophobic, organic substances which are not surface-active.

In the dispersions according to the present invention, the dispersed phase is formed by aromatic isocyanatosulfonic acid uretdiones. The continuous phase is formed by any liquid organic polyisocyanates which are free from sulfonic acid groups. The total number of equivalents of isocyanate groups, including the isocyanate groups of the isocyanatosulfonic acid uretdiones present in dimerized form as uretdione are made up of from 5 to 60 equivalent percent, preferably from 20 to 52 equivalent percent of isocyanate groups or dimerized isocyante groups of the isocyanatosulfonic acid uretdiones and from 40 to 95 equivalent percent preferably from 48 to 80 equivalent percent of isocyanate groups of the non-sulfonated polyisocyanates. In addition, the isocyanatosulfonic acid uretdiones forming the dispersed phase have a mean particle size of less than 0.02 mm, preferably less than 0.01 mm, so that they would not be retained by a sieve of corresponding mesh width.

The aromatic isocyanatosulfonic acid uretdiones present as the dispersed phase in the dispersions according to the present invention are compounds which are solid at room temperature, of the type accumulating in finely divided form during the sulfonation of aromatic diisocyanates or polyisocyanates. The compounds in question are preferably monosulfonation products of aromatic polyisocyanates present in the form of uretdione polyisocyanates and corresponding to the following general formula:

Q (NCO)$_n$ wherein
Q represents an aromatic hydrocarbon radical containing from 6 to 15 carbon atoms and
n represents a whole or fractional number having a value of from 2 to 3.

In accordance with the definition of n as a whole or broken fractional number, it is of course also possible to use polyisocyanate mixtures having a mean NCO-functionality of preferably from 2 to 3. Other suitable isocyanatosulfonic acid uretdiones are the sulfonation products of any substituted, particularly chlorine, bromine, or $C_1$-$C_4$-alkoxysubstituted aromatic polyisocyanates or the sulfonation products of aromatic polyisocyanates containing thioether, carbodiimide, isocyanurate or biuret groups. Examples of suitable aromatic polyisocyanates are 4,4'-stilbene diisocyanate, 4,4'-dibenzyl diisocyanate; 3,3'- or 2,2'-dimethyl-4,4'-diisocyanatodiphenyl methane; 2,5,2'-tetramethyl-4,4'-diisocyanatodiphenyl methane; 3,3'-dimethoxyl-4,4'-diisocyanatodiphenyl methane; 4,4'-diisocyanatodimethyl methane; 4,4'-diisocyanatodiphenyl cyclohexyl methane; 4,4'-diisocyanatobenzophenone; 4,4'-diisocyanatodiphenyl sulfone; 4,4'-diisocyanatodiphenyl ether; 4,4'-diisocyanato-3,3'-dibromodiphenyl methane; 4,4'-diisocyanato-3,3'-diethyl diphenyl methane; 4,4'-diisocyanato-1,2-diphenyl ethylene; 4,4'-diisocyanatodiphenylsulfide; 1,3- and 1,4-phenylene diisocyanate; 2,4-phenylene diisocyanate; 2,4- and 2,6-tolylene diisocyanate and mixtures of these isomers; diphenyl methane-2,4'and/or -4,4'-diisocyanate; naphthylene-1,5-diisocyanate; triphenyl methane-4,4',4''-triisocyanate; polyphenyl polypmethylene polyisocyanates of the type obtained by condensing aniline with formaldehyde, followed by phosgenation (British Pat. Nos. 874,430 and 848,671); aromatic polyisocyanates containing carbodiimide groups (German Pat. No. 1,092,007); aromatic diisocyanates of the type described in U.S. Pat. No. 3,492,330; aromatic polyisocyanates containing allophanate groups (British Pat. No. 994,890); Belgian Pat. No. 761,626; and published Dutch Patent Application No. 7,102,524); aromatic polyisocyanates containing isocyanurate groups (German Pat. Nos. 1,022,789; 1,222,067; and 1,027,394 and German Offenlegungsschriften Nos. 1,929,034; and 2,004,048); aromatic polyisocyanates containing acylated urea groups (German Pat. Nos. 1,230,778) and aromatic polyisocyanates containing biuret groups (German Pat. No. 1,101,394; British Pat. No. 889,050; and French Pat. No. 7,017,514).

It is preferred to use powder-form, sulfonated, dimeric aromatic diisocyanates and triisocyanates, particularly dimeric mono- and di-sulfonic acids, preferably monosulfonic acids, of 4,4'-diisocyanatodiphenyl methane, 2,4'-diisocyanatodiphenyl methane and, in particular, 2,4-diisocyanatotoluene and 2,6-diisocyanatotoluene and also mixtures of these isomers.

The continuous phase of the dispersions according to the present invention is preferably formed by any organic polyisocyanates, the polyisocyanates in question are preferably either liquid at room temperature or can be liquefied by heating to at most, 60° C. and preferably to 40° C. at most. The above-mentioned aromatic polyisocyanates which satisfy these requirements preferably represent the continuous phase. However, aliphatic diisocyanates, such as hexamethylene diisocyanate, trimethyl hexamethylene diisocyanate; or cycloaliphatic diisocyanates such as 1-isocyanato-3,3,5-trimethyl-5-isocyanatomethyl cyclohexane, 1-methyl-2,4-diisocyanatocyclohexane, 1-methyl-2,6-diisocyanatocyclohexane, 4,'-diisocyanatodicyclohexyl methane, and their dimers, trimers, allophanates and biurets, may be used.

It is necessary to use certain auxiliaries in the practical application of the process according to the present invention. These auxiliaries are hydrophobic organic substances which do not contain any hydrophobic substituents inert to isocyanate groups. They should also be soluble in the organic polyisocyanates, at least at an elevated temperature (maximum 150° C.), be solid or liquid at room temperature and contain polar groups and, optionally, isocyanate-reactive groups. Substances of this type include:

1. Predominantly non-crystalline polymers satisfying the above-mentioned requirements such as polyvinyl chloride, polyvinylidene chloride, polyvinylacetate, polyacrylates, polycarbonates, cellulose esters, polypropylene, polyesters, polyethers, polyurethanes, polystyrene, and copolymers (such as styrene/acrylonitrile/acrylate copolymer, polyester, urethane, ureas, and polyvinyl pyrrolidone). The molecular weights of suitable polymers are generally in the range of from 4000 to 500,000, preferably in the range of from 10,000 to 200,000. PVC is particularly preferred.

2. Compounds which correspond to the general definition given above and which have the following general formula:

R—X wherein R represents a straight-chain or branched-chain aliphatic, cycloaliphatic or aromatic hydrocarbon radical containing from 6 to 30 carbon atoms of which the hydrogen atoms may be completely or partly substituted by halogen atoms, particularly fluorine, chloride or bromine; and X represents —OH, —O—(CH$_2$CH$_2$—O—)$_n$—H, —SH, —COOH, —NH$_2$, —NHR$^1$, —NR$^1$R$^2$,

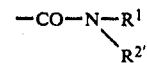

—NCO, —(Y)$_{0-1}$—CO—NH—Ar, (Y)$_{0-1}$—CO—N-H—Ar—NCO, or —NH—CO—Y—R$^1$ wherein R$^1$ and R$^2$, which may be the same or different, represent C$_1$-C$_4$-alkyl radicals which may be substituted by —OH, —O—(CH$_2$CH$_2$O)$_n$H, —SH, —Y—CO—N-H—Ar or —Y—CO—NH—Ar or —Y—CO—N-H—Ar—NCO;

Y represents —O—,—S—,—NH or —NR$^1$—;

Ar represents a radical of the type obtained by removing an isocyanate group from a monoisocyanate having a molecular weight in the range of from 57 to 180 or by removing one or two NCO-groups from an organic polyisocyanate having a molecular weight in the range of from 168 to 300, and n represents 1 or 2.

Examples of suitable compounds of group (2) are: alcohols and thioalcohols, such as 1-hexanol, 4-methyl-2-pentanol, 2-ethyl-1-butanol,1-octanol, 2-ethyl-1-hexanol, 1-nonanol, trimethyl-1-hexanol, 1-decanol, 1-dodecanol,1-dodecane thiol, 1-tetradecanol, 1-hexadecanol, 1-octadecanol, also commercial alcohol mixtures such as "lorol" ($C_{12}H_{26}O$—$C_{18}H_{38}O$), "alfol" ($C_{14}H_{30}O$—$C_{22}H_{46}O$), methyl cyclohexanol, cyclohexane methanol, trimethyl cyclohexanol, benzyl alcohol, 2-hydroxy decalin, and 4-tert.-butyl cyclohexanol; phenols such as ethyl phenol, xylenol, chloroxylenol, isopropyl phenyl, sec.-butyl phenol, tert.-butyl phenol, thymol, 4-(1,1-dimethylpropyl)-phenol, trichlorophenol,trichlorocresol, 4-(1,1,3,3-tetramethyl-butyl)-phenol,nonyl phenol, di-tert.-butylphenol, di-tert.-pentyl phenol, dodecyl phenol, cyclohexyl phenol, naphthol,phenyl phenol, 4-hydroxydiphenyl, benzylphenol,-cumyl phenol and also isomer mixtures and commercial mixtures of the above-mentioned phenyls; carboxylic acids such as 2-ethyl hexanoic acid, coconut oil fatty acid first runnings, coconut oil fatty acid, versatic acid, lauric acid, myristic acid, palmitic acid, stearic acid and also commercial mixtures of these carboxylic acids, tolylic acid, tert.-butyl benzoic acid, and naphthoic acid; amines such as 2-ethyl hexylamine, bis-(2-ethyl-hexyl)-amine, dodecylamine, tetradecylamine, hexadecylamine, octadecylamine, methyl octadecylamine, N-methyl cyclohexylamine, N-ethyl cyclohexylamine, dicyclohexylamine, methyl cyclohexylamine, trimethyl cyclohexylamine, N-ethyl aniline, N-butyl aniline, N-isobutyl aniline, dioxethyl-m-toluidine, benzyl aniline, O-tolyl benzylamine, dibenzylamine xylidine, 3,5-bistrifluoromethyl aniline, isopropyl aniline, ethylmethyl aniline, tert.-butyl aniline, diethyl aniline, diethyl butyl aniline, diisopropyl aniline, dodecyl aniline, 4-cyclohexyl aniline, 1-naphthylamine, N-ethyl-1 naphthylamine, and cyclohexylamine; and isocyanates such as 6-chlorohexyl isocyanate, 2,6-diisopropyl phenyl isocyanate, dodecyl isocyanate,tetradecyl isocyanate, hexadecyl isocyanate, naphthyl isocyanate and stearyl isocyanate.

Other compounds of group (2) are, for example, coconut oil fatty acid amide, lauric acid amide, stearylamide, stearic acid dimethyl amide, dodecyl diethanolamine, oleyl diethanolamine, stearyl diethanolamine, stearyl diisopropanolamine, dodecyl sulfonic acid, naphthaline monosulfonic acid, xylene sulfonic acid, biphenyl sulfonic acid, pyrene sulfonic acid, sulfonated $C_8$-$C_{30}$- hydrocarbons and also adducts of the above-mentioned alcohols, amino-alcohols, phenols, mercaptans, carboxylic acids, amines and amides with mono-, di or poly-isocyanates.

3. Substituted hydrocarbons which correspond to the general definition given above and which have the following general formula:

R—Z—R' wherein

R represents a straight-chain or branched-chain aliphatic, cycloaliphatic or aromatic hydrocarbon radical containing from 6 to 30 carbon atoms of which the hydrogen atoms may be completely or partly substituted by halogen atoms, particularly fluorine, chloride or bromine, and R' represents an optionally halogen-substituted, preferably fluorine-, chlorine- or bromine-substituted, hydrocarbon radical containing from 1 to 18 carbon atoms and Z represents a —CO—, —SO$_2$—, —NHCONH—, NHCOO—, —NHCO—, —NHCSNH—, —NH— or —CHOH— group.

Examples of suitable compounds of group (3) are dicyclohexyl ketone, ditolyl ketone, acetophene, p-chloroacetophenone, 2-undecanone, 10-nonadecanone, 1,1,3-trimethyl-5-cyclohexanone, cyclododecanone, bis-dodecyl urea,bis-stearyl urea, N-phenyl-N'-stearyl urea, N-stearyl ethyl urethane, N-methyl stearyl urethane, distearyl amide, bis-stearyl(thio) urea, dicyclohexylamine, didodecylamine, distearylamine, 2-undecanol, and 10-nonadecanol. It is preferred to use adducts of isocyanates with alcohols and carboxylic acids.

4. Adducts of organic monoisocyanates, particularly aliphatic monoisocyanates having a molecular weight in the range of from 155 to 295, and polyalcohols, polyamines or polycarboxylic acids, particularly aliphatic polyalcohols having a molecular weight in the range of from 62 to 300, which correspond to the general definition given above, but which do not come under the general formula given in (2) and adducts of polyisocyanates having a molecular weight in the range of from 168 to 300 with monohydric alcohols, monoamines or monocarboxylic acids, particularly monohydric aliphatic alcohols having a molecular weight in the range of from 32 to 200, which do not come under the general formula given in (2). The adducts should preferably contain at least one aliphatic hydrocarbon chain having from 8 to 30 carbon atoms. Examples of adducts such as these are the reaction products of:

1 mole of TDI+2 moles of stearyl alcohol,
1 mole of TDI+1 mole of dodecanol+1 mole of methnoal,
1 mole of MDI+1.8 moles of 2-ethyl hexanol,
1 mole of BTI+2 moles of lauric acid+1 mole of butanol,
1 mole of HDI=2 moles of palmitic acid,
1 mole of TMP+3 moles of stearyl isocyanate,
1 mole of TMP+2 moles of stearyl isocyanate,
1 mole of GLY+1 mole of stearyl isocyanate,
1 mole of TMP+1 mole of stearyl isocyanate, +2 moles of 6-chlorohexyl isocyanate,
1 mole of HD+1.5 moles of lauryl isocyanate,
1 mole of AD+2 moles of stearyl isocyanate,
1 mole of WS+2 moles of stearyl isocyanate, the above abbreviations being defined as below:
TDI:2,4-tolylene diisocyanate,
MDI:4,4'-diisocyanatodiphenyl methane,
HDI:1,6-diisocyanatohexane,
BTI:tris-(6-isocyanatohexyl)-biuret,
TMP:trimethylol propane,
GLY:glycerol,
HD:1,6-hexane diol,
AD:adipic acid,
WS:tartaric acid.

5. Other organic compounds which correspond to the general definition given above such as acetophenone, diphenyl sulfone, adipic acid dimethyl ester, phthalic acid dioctyl ester or benzophenone.

In the process according to the present invention, the auxiliaries mentioned by way of example above in (1) to (5) are used in a quantity of from 0.2 to 25% by weight, preferably in a quantity of from 1 to 10% by weight and, more particularly, in a quantity of from 2 to 6% by weight, based on the total quantity of sulfonated and non-sulfonated polyisocyanates present.

The process according to the present invention for producing the dispersions according to the invention is preferably carried out in accordance with one of the following embodiments (a), (b), or (c).

Embodiment (a)

An aromatic polyisocyanate or polyisocyanate mixture of the type mentioned by way of example above is sulfonated by a known method (cf. for example, U.S. Pat. No. 3,826,769, German Offenlegungsschriften Nos. 2,524,476 or 2,615,876) at a temperature in the range of from −20° to 100° C., preferably at a temperature in the range of from 0° to 60° C. and, most preferably, at a temperature in the range of from 10° to 40° C., at least one of the auxiliaries mentioned by way of example in (1) to (5) being added before or during sulfonation. Sulfonation is accompanied by intensive stirring. Sulfur trioxide or a sulfonating agent, containing or forming sulfur trioxide is used for sulfonation in such a quantity that from 0.05 to 0.6 moles, preferably from 0.2 to 0.52 moles of sulfur trioxide are active per mole of aromatic polyisocyanate to be sulfonated. In this way, a dispersion corresponding to the present invention is directly formed.

Embodiment (b)

An aromatic polyisocyanate or polyisocyanate mixture of the type mentioned by way of example above is sulfonated by a known method (for example, in accordance with German Offenlegungsschrift No. 2,615,876) in the presence of one of the auxiliaries essential to the present invention mentioned above in (1) to (5) in the quantities indicated, in an inert, low-boiling organic solvent such as methylene chloride, dichloroethane, chloroform or tetrachloroethane at a temperature in the range already mentioned in (a). From 0.2 to 2.0 moles, preferably from 0.3 to 1.2, moles of sulfur trioxide are used per mole of aromatic polyisocyanate to be sulfonated. The solvent is then removed by distillation. If more than 0.6 moles of sulfur trioxide is used per mole of polyisocyanates, an organic polyisocyanate forming the major part of the continuous phase is added before removal of the solvent by distillation in such a quantity that, ultimately, the content of aromatic isocyanatosulfonic acid uretdione in the dispersion obtained corresponds to the figures indicated above. The polyisocyanate forming the continuous phase should be either liquid at room temperature or liquefiable simply by heating to, at most, 60° C., preferably to 40° C. at most. In this embodiment, the aromatic polyisocyanate used for sulfonation may have a melting point above 60° C.

In both embodiments (a) and (b), the preferred aromatic polyisocyanates mentioned by way of example above are preferably used both for sulfonation and also as the continuous phase.

Embodiment (c)

This embodiment of the process according to the present invention uses coarse suspensions of aromatic isocyanatosulfonic acid uretdiones in aromatic polyisocyanates or in the readily volatile inert solvents already mentioned by way of example. Coarse suspensions such as these are obtained by sulfonating aromatic polyisocyanates in known manner (cf. for example, U.S. Pat. No. 3,826,769; German Offenlegungsschriften Nos. 2,524,476 or 2,615,876) or even by suspending powder-form aromatic isocyanatosulfonic acid uretdiones obtained in accordance with the prior art in liquid polyisocyanates and/or inert solvents. After the auxiliaries essential to the present invention, as mentioned by way of example in (1) to (5), have been added to these coarse suspensions in the quantities indicated, the suspensions are heated as briefly as possible to at most 150° C. until a solution is formed.

Thereafter, they are rapidly cooled or subjected to grinding. After grinding or during the heat treatment, the auxiliary solvent used, if any, is removed by distillation. In the absence of non-sulfonated polyisocyanates, a liquid polyisocyanates of the type already described which forms the continuous phase is added before removal of the solvent by distillation. In order to avoid substantially unknown secondary reactions, it is favorable to keep the heating time as short as possible, for example, between 2 minutes and about 2 hours, preferably between 2 minutes and about 30 minutes. For this reason, heating should be carried out as quickly as possible. In addition, the temperature should not rise above the level absolutely essential for forming a temporary solution. In no case should a maximum temperature of 150° C. be exceeded. The maximum temperature briefly required for the formation of a solution is preferably between 80° and 120° C. Heating and, in particular, cooling, should be accompanied by stirring or mechanical agitation.

In the event of continuous operation, it is favorable to use heat exchangers in a heating zone with a short residence time.

The above-mentioned grinding of the coarse suspensions in the presence of the auxiliaries essential to the present invention may be carried out in addition to, or even instead of, the increase in temperature. This measure is intended to reduce the particle size of the suspended aromatic isocyanatosulfonic acid uretdiones to less than 0.02 mm and is particularly necessary in the case of high concentrations of solid isocyanatoaryl sulfonic acid uretdione where it is not possible to form a solution by heating at a temperature below 150° C. In addition, it may be carried out in the presence of aromatic dispersion media, such as toluene, chlorobenzene, TDI or MDI.

Fine dispersion by heating and recooling is preferably applied in the presence of aliphatic dispersion media, such as, in particular, in the presence of aliphatic polyisocyanates.

In embodiment (c) of the process according to the present invention, it is advantageous to use polymers, particularly PVC powders, as the auxiliaries used in accordance with the invention, whereas in embodiment (b) of the process, the use of these auxiliaries is only advisable in cases where the sulfonating agent is used in a deficit in relation to the polyisocyanate to be sulfonated because otherwise color darkening occurs.

Embodiments (b) and (c) of the process where the polyisocyanate forming the continuous phase is subsequently added are particularly suitable for the production of dispersions in aliphatic polyisocyanates. Because of the satisfactory toxicology of these aliphatic polyisocyanates, coupled with the fact that their liquid aggregate state makes them easy to handle, dispersions of this type are of particular interest.

In cases where auxiliaries essential to the present invention containing isocyanate-reactive groups are used, it is best, although not necessary, to react them with polyisocyanate before carrying out the process measures according to the invention, and in particular before carrying out the sulfonation reaction corresponding to embodiments (a) and (b). The urethane, urea and amide isocyanates formed from these auxiliaries, for example, the alcohols, amines or carboxylic acids mentioned by way of example, are particularly effective auxiliaries.

The described embodiments (a), (b), and (c) of the process may of course also be combined. For example, TDI may be sulfonated in the presence of stearyl isocyanate, the finely divided suspension may be subsequently heated briefly with polyvinyl chloride powder and/or a mixture of fatty alcohols (dissolution is not necessary because the suspension is already finely divided) and cooled again with stirring. Since in this way neither the PVC nor the fatty alcohol mixture comes into direct contact with the sulfonating agent a particularly light product is obtained.

A particularly light-colored suspension of aromatic isocyanatosulfonic acid uretdiones in aliphatic polyisocyanates is correspondingly obtained by carrying out sulfonation of the aromatic isocyanate in the presence of stearyl isocyanate and/or a urethane obtained from aliphatic isocyanate and a mixture of fatty alcohols or benzyl alcohol, subsequently adding the aliphatic isocyanate containing from 1 to 5% of PVC and then distilling off the solvent used, if any.

The addition of the auxiliaries essential to the present invention mentioned by way of example in (1) to (5), which do not have any surface-active properties, greatly reduces the particle size of the isocyanatosulfonic acids formed so that non-sedimenting dispersions can be obtained.

In particular, it is possible by the process according to the present invention to produce finely divided non-sedimenting dispersions of dimeric diisocyanatotoluene sulfonic acid in diisocyanatotoluene and of dimeric diisocyanatodiphenyl methane sulfonic acid in diisocyanatodiphenyl methane. This is of considerable importance to the handling of dispersions such as these. The sulfonic acids are uniformly distributed in the dispersions which can be exactly metered and, because of the large particle surface, provide for a fast reaction, for example, with cyclic ethers on the sulfonic acid group and with compounds containing active hydrogen atoms on the isocyanate group. As already mentioned, the dispersed isocyanatoaryl sulfonic acid uretdiones have mean particle diameters of less than 0.02 mm and preferably less than 0.01 mm. In many cases, diameters of from 0.0004 to 0.008 mm are obtained. In contrast, the diameters of the particles of coarse suspensions obtained in accordance with the prior art generally lie between 0.05 and 0.5 mm.

The dispersions according to the present invention are non-sedimenting, i.e., no significant sedimentation occurs over a period of 24 hours, whereas dispersions according to the prior art generally show distinct sedimentation after only 0.5 hours. As will be shown in the Examples, dispersions which, even after 6 months, show only minimal sedimentation are obtained in many cases.

Preferred dispersions according to the present invention include dispersions of dimerized diisocyanatotoluene sulfonic acid in diisocyanatotoluene or diisocyanatodiphenyl methane, dispersions of dimeric, monosulfonated diisocyanatodiphenyl methane in diisocyanatodiphenyl methane and dispersions of the above-mentioned aromatic isocyanatosulfonic acid uretdiones in the liquid aliphatic and cycloaliphatic diisocyanates mentioned by way of example above.

In the context of the present invention, "diisocyanatoaryl sulfonic acid uretdiones" are understood to be products of the type which accumulate in solid crystalline form in sulfonation of predominantly pure aromatic polyisocyanates of their isomer mixtures. They may also contain sulfonic acid anhydrides. Diisocyanatodiphenyl methanes (dispersion medium) are understood to be not only the more or less pure binuclear products, but also the so-called MDI polymer types, i.e., any phosgenation products of aniline formaldehyde condensates; also correspondingly synthesized products of the type obtained for example by splitting phenyl urethane/formaldehyde condensation products or by the process according to German Offenlegungsschrift No. 2,709,490.

The dispersions according to the present invention may be used as new starting materials for the production of isocyanate-polyaddition products and, in particular, for the production of polyurethanes in compact and foamed form.

They enable solid, highly sulfonated isocyanates to be used in the processing-favorable form of liquid products. Polyurethanes and polyurethane ureas produced therefrom show greatly improved non-inflammability. In reactions with oxiranes, oxetanes, tetrahydrofuran and caprolactone, the large surface of the dispersed sulfonic acid provides for high reaction velocities of the level required for the production of foams.

Dispersions of aromatic isocyanatosulfonic acid uretdiones in aliphatic polyisocyanates of low vapor pressure are isocyanate systems which are non-toxic and environmentally acceptable in every respect.

In the following Examples, all the precentages quoted represent % by weight, unless otherwise indicated.

EXAMPLE 1

522 g (3.0 moles) of "TDI 80" (isomer mixture of 80% of 2,4-diisocyanatotoluene and 20% of 2,6-diisocyanatotoluene) are stirred for 4 hours at 50° C. with 26.2 g (0.1 mole) of a commercial fatty alcohols mixture (2% of $C_4H_{29}OH$, 51% of $C_{16}H_{33}OH$, 28% of $C_{18}H_{37}OH$, 14% of $C_{20}H_{41}OH$, 3% of $C_{22}H_{45}OH$; m.p. 43°–47° C., b.p. 318° C.). 115 g (1.44 moles) of sulfur trioxide are introduced with stirring at from 25° to 30° C., resulting in the formation of a very finely divided, macroscopically homogeneous dispersion of the sulfonic acid uretdione in excess TDI 80 in the form of a spreadable paste. No sedimentation occurs over a period of 6 months. Content of sulfonic acid uretdione: 365 g=55%; content of free and dimerized isocyanate groups in the sulfonated diisocyanate, based on the total of all isocyanate groups: 48 equivalent %.

COMPARISON EXAMPLE

If the same test is carried out in the absence of the fatty alcohol, a coarse suspension of the sulfonic acid uretdione is obtained, which sediments in a matter of hours.

EXAMPLE 2

522 g (3.0 moles) of TDI 80 are stirred with 7.8 g (1.5%) of standard commercial-grade polyvinyl chloride powder at 110° C. until the PVC has dissolved. Immediately after cooling to 22° C., 73 g (0.9 mole) of sulfur trioxide are introduced with stirring, resulting in the formation of a very finely divided dispersion of the sulfonic acid uretdione in excess TDI 80. After 6 months, the dispersion has thickened, but has not sedimented. Some dilation is observed on stirring. Sulfonic acid uretdione content 230 g =38%; content of free and dimerized isocyanate groups of the sulfonated diisocyanate, based on the total of all isocyanate groups: 30 equivalent %.

EXAMPLE 3

522 g (3.0 moles) of TDI 80 are stirred for 30 minutes at from 22° to 27° C. with 22.8 g (0.1 mole) of a commercial fatty alcohol mixture of $C_{12}H_{25}OH$, $C_{14}H_{29}OH$, $C_{16}H_{33}OH$ and $C_{18}H_{37}OH$. After this, 114 g (1.43 moles) of sulfur trioxide are introduced, resulting in the formation of a predominantly very finely divided macroscopically homogeneous dispersion in the form of a spreadable paste. Sulfonic acid uretdione content: 362 g=55%; content of free dimerized isocyanate groups of the sulfonated diisocyanate, based on the total of all isocyanate groups, 48 equivalent %.

EXAMPLE 4

64 g (0.8 mole) of sulfur trioxide are introduced at from 20° to 30° C. into a stirred mixture of 522 g (3.0 moles) of TDI 80 and 29.5 g (0.1 mole) of stearyl isocyanate, resulting in the formation of a very finely divided thixotropic dispersion in the form of a paste. After 7 months, no sedimentation has occured. Content of free and dimerized isocyanate groups of the sulfonated diisocyanate, based on the total of all isocyanate groups: 27 equivalent %.

EXAMPLE 5

12.5 g of standard commercial-grade polyvinyl chloride powder were dissolved in 500 ml of 1,2-dichloroethane. 250 g (1.0 mole) of 4,4'-diisocyanatodiphenyl methane and 14.7 g (0.05 mole) of stearyl isocyanate are then added and also dissolved. 80 g (1 mole) of sulfur trioxide are then introduced with stirring at from 26° to 30° C., resulting in the formation of a very finely divided dark dispersion. After 6 months, only slight sedimentation has occurred. Complete homogenization can be rapidly obtained by stirring. Sulfonic acid uretdione content: 33.6%. 100 g of the dispersion in dichloroethane are mixed with 80 g of hexamethylene diisocyanate, after which the dichloroethane is distilled off under reduced pressure at 50° C. A finely divided dispersion of the isocyanatosulfonic acid uretdione in hexamethylene diisocyanate having a solids content of 29% is obtained.

EXAMPLE 6

5.3 g of N-oleyl diethanolamine are added dropwise to 261 g (1.5 moles) of TDI 80, urethanization occurring with an increase in temperature. 39 g (0.49 mole) of sulfur trioxide are then introduced for sulfonation, resulting in the formation of a very finely divided dispersion which, after 6 months, has only slightly sedimented and may readily be redispersed. Sulfonic acid uretdione content: 124 g=40.5 % content of free and dimerized isocyanate groups of the sulfonated diisocyanate, based on the total quantity of all isocyanate groups: 33 equivalent %.

EXAMPLE 7

The procedure is as described in Example 2, except that 4 g of a high molecular weight standard commercial-grade polycarbonate are used instead of PVC. The dispersion is passed through a fine metal sieve and is thus freed from coarse-grained fractions. The filtrate is a finely divided dispersion.

EXAMPLE 8

The procedure is as described in Example 2, except that 4 g of a standard commercial-grade high molecular weight polystyrene are used. A thinly liquid finely divided dispersion which only sediments slowly is obtained. The deposit precipitated may be very easily redispersed.

EXAMPLES 9 to 23

In a series of orienting tests, a number of substances were tested for their emulsifying and stabilizing effect in the sulfonation of tolylene diisocyanate. To this end, 20 g of TDI 80 were mixed with 2 g of the substance to be tested and the resulting mixture was mixed in a test tube with 5 ml of a 26% solution of sulfur trioxide in dichloroethane. Since sulfonation occurs almost instantaneously without stirring, the deposits precipitate in a relatively coarse-grained form and sediment quickly. A sediment is also obtained using stearyl isocyanate under these conditions, although in this case it is finely divided and may very easily be redispersed. Good results, i.e., finely divided slowly sedimenting and readily redispersible deposits are obtained with:

9. dodecanol
10. stearylisocyanate
11. nonyl phenol
12. dicyclohexylamine
13. coconut oil fatty acid
14. stearic acid
15. naphthoic acid
16. cyclohexyl phenol
17. tert.-butyl phenol
18. trichlorophenol
19. 2-ethyl-1-hexanol
20. 1-hexanol
21. acetophenone
22. benzyl alcohol
23. stearyl isocyanate+benzyl alcohol (deposit does not sediment).

Under the conditions of Example 1, these substances give very finely divided non-sedimenting or only slowly sedimenting dispersions.

EXAMPLE 24

2 g of benzyl alcohol are added to a solution of 0.3 g of PVC powder in 20 g of TDI 80, urethanization occurring over a period of 1 hour. The addition of 10 ml of a 26% solution of sulfur trioxide in dichloroethane gives a very finely divided dispersion which does not sediment over a period of 48 hours.

EXAMPLE 25

100 g of 1,6-diisocyanatohexane and 5 g of PVC powder are heated with stirring until the PVC has completely passed into solution. 20 g of the uretdione of 2,4-diisocyanatotoluene-5-sulfonic acid are introduced at from 100° to 130° C. and dissolved with stirring. After the solution has cooled, a very finely divided non-sedimenting dispersion is obtained.

EXAMPLE 26

174 g (1.0 mole) of TDI 65, 15 g of stearyl isocyanate and 5 g of benzyl alcohol are dissolved in 250 ml of 1,2-dichloroethane, 80 g (1 mole) of sulfur trioxide are introduced at from 10° to 20° C. resulting in the formation of a very finely divided white dispersion. 350 g of a 5% solution of PVC in 1,6-diisocyanatohexane are then stirred in and the dichloroethane is distilled in in vacuo, leaving a white very finely divided non-sedimenting dispersion. Uretdione sulfonic acid content: 39%.

EXAMPLE 27

The procedure is as described in Example 26, except that isophorone diisocyanate is used instead of 1,6-diisocyanatohexane. The white isocyanate dispersion obtained is very easy to handle, does not cause any irritation to mucosa by giving off vapors at room temperature and does not form any aromatic diamines on hydrolytic degradation of the plastics produced therefrom.

EXAMPLE 28

TDI 80 is sulfonated as described in Example 24 in the presence of 15% of 6-chlorohexylisocyanate. A finely divided dispersion which does not sediment over a period of 24 hours is obtained.

EXAMPLE 29

20 g of the uretdione of 2,4-diisocyanatotoluene-5-sulfonic acid are heated to 140° C. in solution in 100 g of isophorone diisocyanate containing 1% of PVC, resulting in the formation of a clear solution which is rapidly cooled with stirring to room temperature. A very fine opaque-white non-sedimenting dispersion is formed. A corresponding product is obtained when 2% of "alfol 1620" (cf. Example 1) is used instead of PVC. The dispersion is stable in storage for several months.

What is claimed is:
1. Non-sedimenting dispersions in organic polyisocyanates comprising: finely divided solid aromatic isocyanatosulfonic acid uretdiones having a mean particle size of less than 0.02 mm which are liquid at room temperature or may be liquefied by heating to at most 60° C. and which contain a total of from 5 to 60 equivalent % of free and dimerized isocyanate groups of aromatic polyisocyanatosulfonic acids, based on the total number of equivalents of isocyanate groups.

2. The dispersions of claim 1, wherein diisocyanatotoluene sulfonic acid uretdione forms the disperse phase and diisocyanatotoluene and/or diisocyantodiphenyl methane forms the continuous phase.

3. The dispersions of claim 1, wherein diisocyanatodiphenyl methane sulfonic acid uretdione forms the disperse phase and diisocyanatodiphenyl methane forms the continuous phase.

4. A process for producing dispersions comprising: sulfonating an aromatic polyisocyanate with from 5 to 60 mole % of sulfur trioxide or with a corresponding quantity of a sulfonating agent containing or forming sulfur trioxide in the presence of from 0.2 to 25% by weight, based on the weight of the polyisocyanate, of a hydrophobic organic substance which does not contain any hydrophilic substituents inert to isocyanate groups, is soluble in isocyanates, at least at an elevated temperature, is solid or liquid at room temperature and contains polar groups and, optionally contains isocyanate-reactive groups.

5. The process of claim 4, wherein said aromatic polyisocyanate is selected from the group consisting of 4,4'-diisocyanatodiphenyl methane, 2,4'-diisocyanatodiphenyl methane, 2,4-diisocyanatotoluene, 2,6-diisocyanatotoluene, and mixtures thereof.

6. A process for producing dispersions comprising:
(A) Sulfonating an aromatic polyisocyanate with from 20 to 200 mole % of sulfur trioxide or with a corresponding quantity of a sulfonating agent containing or forming sulfur trioxide in the presence of from 0.2 to 25% by weight, based on the weight of the polyisocyanate of a hydrophobic organic substance in inert low-boiling organic solvents, wherein said hydrophobic organic substance does not contain any hydrophilic substituents inert to isocyanate groups, is soluble in isocyanates at least at elevated temperatures, is solid or liquid at room temperature and contains polar groups and, optionally, isocyanate-reactive groups, and thereafter
(B) removing the solvent by distillation, said aromatic polyisocyanate forming the major part of the continuous phase being added before removal of the solvent by said distillation in cases where more than 60% of said sulfur trioxide is used per mole of said aromatic polyisocyanate.

7. The process of claim 6, wherein said aromatic polyisocyanate is selected from the group consisting of 4,4'-diisocyanatodiphenyl methane, 2,4'-diisocyanatodiphenyl methane, 2,4-diisocyanatotoluene, 2,6-diisocyanatotoluene, and mixtures thereof.

8. A process for producing dispersions comprising:
(A) briefly heating unstable coarse suspensions of aromatic isocyanatosulfonic acid uretdiones in non-sulfonated polyisocyanates or inert solvents to at most 150° C. in the presence of from 0.2 to 25% by weight, based on the total quantity of isocyanate, of a hydrophobic organic substance until a solution is formed, wherein said hydrophobic organic substance does not contain any hydrophilic substituents inert to isocyanate groups, is soluble in isocyanates at least at elevated temperature, is solid or liquid at room temperature and contains polar groups and, optionally, isocyanate-reactive groups; and
(B) rapidly cooling and/or grinding said solution and removing by distillation said inert solvents used, if any, and in cases where coarse suspensions which do not contain any non-sulfonated polyisocyanates are used, organic polyisocyanate is added to form the continuous phase before removal of the solvent by distillation; and wherein the quantity of said aromatic isocyanatosulfonic acid uretdione and said non-sulfonated polyisocyanate are such that the stable dispersions ultimately obtained contain a total of from 5 to 60 equivalent % of free and dimerized isocyanate groups of said isocyanatosulfonic acid uretdione, based on the total number of equivalents of isocyanate groups.

9. The process of claim 8, wherein said aromatic polyisocyanate is selected from the group consisting of 4,4'-diisocyanatodiphenyl methane, 2,4'-diisocyanatodiphenyl methane, 2,4-diisocyanatotoluene, 2,6-diisocyanatotoluene, and mixtures thereof.

* * * * *